(12) United States Patent
Hogendijk

(10) Patent No.: US 6,632,236 B2
(45) Date of Patent: Oct. 14, 2003

(54) CATHETER HAVING RADIALLY EXPANDABLE MAIN BODY

(75) Inventor: Michael Hogendijk, Palo Alto, CA (US)

(73) Assignee: Arteria Medical Science, Inc.

( * ) Notice: Subject to any disclaimer, the term of this patent is extended or adjusted under 35 U.S.C. 154(b) by 79 days.

(21) Appl. No.: 09/916,349

(22) Filed: Jul. 26, 2001

(65) Prior Publication Data

US 2002/0022859 A1 Feb. 21, 2002

Related U.S. Application Data

(63) Continuation-in-part of application No. 09/418,727, filed on Oct. 15, 1999, now Pat. No. 6,423,032, which is a continuation-in-part of application No. 09/333,074, filed on Jun. 14, 1999, now Pat. No. 6,206,868, which is a continuation-in-part of application No. PCT/US99/05469, filed on Mar. 12, 1999.

(51) Int. Cl.⁷ ............................................. A61M 29/00
(52) U.S. Cl. .................................................... 606/198
(58) Field of Search ................................ 606/200, 195, 606/198, 193, 127; 623/1.11, 1.12, 1.2

(56) References Cited

U.S. PATENT DOCUMENTS

| | | | |
|---|---|---|---|
| 4,921,478 A | | 5/1990 | Solano et al. |
| 5,011,488 A | | 4/1991 | Ginsburg |
| 5,064,435 A | * | 11/1991 | Porter ........................ 623/1.11 |
| 5,102,401 A | | 4/1992 | Lambert et al. |
| 5,102,415 A | | 4/1992 | Guenther et al. |
| 5,549,626 A | | 8/1996 | Miller et al. |
| 5,669,927 A | | 9/1997 | Boebel et al. |
| 5,695,499 A | * | 12/1997 | Helgerson et al. ........... 606/198 |
| 5,702,418 A | * | 12/1997 | Ravenscroft ................ 623/1.11 |
| 5,895,399 A | | 4/1999 | Barbut et al. |
| 5,997,557 A | | 12/1999 | Barbut et al. |
| 6,206,868 B1 | | 3/2001 | Parodi |

* cited by examiner

Primary Examiner—Kevin T. Truong
(74) Attorney, Agent, or Firm—Luce, Forward, Hamilton & Scripps (57) ABSTRACT

Apparatus for occluding a vessel and enhancing blood flow within a catheter are provided, wherein a catheter comprises a multi-section self-expanding wire weave forming a radially expandable body and an occlusive distal section, covered with an elastomeric polymeric coating, and disposed within an outer sheath. Methods of using the apparatus of the present invention to remove emboli also are provided.

20 Claims, 6 Drawing Sheets

CATHETER HAVING RADIALLY EXPANDABLE MAIN BODY

REFERENCE TO RELATED APPLICATIONS

The present application is a continuation-in-part of U.S. patent application Ser. No. 09/418,727, filed Oct. 15, 1999, now U.S. Pat. No. 6,423,032 which is a continuation-in-part of U.S. patent application Ser. No. 09/333,074, filed Jun. 14, 1999, now U.S. Pat. No. 6,206,868 which is a continuation-in-part of International Application PCT/US99/05469, filed Mar. 12, 1999.

FIELD OF THE INVENTION

The present invention relates to apparatus and methods for protecting against embolization during vascular interventions and improving flow characteristics within a catheter. More particularly, the apparatus and methods of the present invention facilitate blood flow within a catheter by providing a catheter having a radially expandable main body section.

BACKGROUND OF THE INVENTION

Catheters are commonly manufactured using materials that do not substantially change in cross-sectional area. It is highly desirable that the initial cross-sectional catheter area be relatively small compared to the vasculature for patient comfort and ease of transluminal guidance. However, catheters in which the working diameters remain relatively small have several disadvantages during interventional procedures.

A primary disadvantage of a small cross-sectional catheter area is increased flow resistance within the catheter. A high volume of blood flow being forced through a relatively small lumen may cause damage to blood cells. During interventional procedures involving the removal of emboli, the flow may be further constrained when aspirating large emboli in addition to blood. It therefore would be advantageous to provide a catheter having a small delivery cross-sectional area for transluminal insertion, but which is capable of expanding to a larger cross-sectional area, thus reducing flow resistance within the catheter.

Heretofore, no reliable expandable catheters have been available. U.S. Pat. No. 5,102,401 to Lambert et al. describes a catheter comprising a thermoplastic elastomeric hydrophilic polyurethane coated on at least the outside surface with a hydrophobic polymer. The catheter expands to a larger lumen size in about 3 to 15 minutes when contacted with an aqueous liquid. Additional publications have further discussed catheters which soften upon being raised to a temperature approaching body temperature.

There are several drawbacks associated with such previously known expandable catheters. Such catheters can soften when deployed, resulting in kinking or deformation of the proximal section of the catheter, thereby cutting off flow. Additionally, such catheters require a wait of up to several minutes for the desired expansion to occur. Accordingly, there remains a need for a structurally durable, rapidly expandable catheter.

Previously-known apparatus and methods are known that employ a mechanically expandable occlusive element disposed at the distal end of a catheter. Commonly assigned U.S. Pat. No. 6,206,868 to Parodi discloses an occlusive element comprising a self-expanding wire mesh basket covered with an elastomeric polymer coating. The catheter is initially surrounded by a movable sheath, and is inserted transluminally with the sheath at a distalmost position. The sheath is retracted proximally to cause the basket to deploy, and the basket is again collapsed within the sheath by moving the sheath to its distalmost position.

The occlusive basket described in the Parodi patent is advantageous because it provides a rapidly expandable basket that is substantially flush with the vessel wall to enhance emboli removal. However, emboli then may be funneled into a relatively small cross-sectional area lumen that extends from the site of the stenosis to the vascular entry site. For many procedures, this distance may comprise the vast majority of the overall catheter length. Accordingly, blood flow is potentially constrained throughout the majority of the catheter.

In view of these drawbacks of previously known catheters, it would be desirable to provide apparatus and methods for radially varying the size of a catheter so that the catheter can be maneuvered within the body at a contracted delivery diameter and then self-expands to a larger diameter to facilitate blood flow.

It also would be desirable to provide apparatus and methods for enhancing the flow of blood and emboli within a catheter by expanding the cross-sectional area of the catheter that extends from the site of the stenosis to the vascular entry site.

It still further would be desirable to provide apparatus and methods for rapidly expanding the cross-sectional area of a catheter without relying on chemical or thermal transformations.

It still further would be desirable to provide apparatus and methods for an expandable catheter whereby the structural integrity is not compromised upon expansion.

It still further would be desirable to provide apparatus and methods for efficiently removing emboli by means of an occlusive member that is substantially flush with the vessel wall.

SUMMARY OF THE INVENTION

In view of the foregoing, it is an object of the present invention to provide apparatus and methods for radially varying the size of a catheter so that the catheter can be maneuvered within the body at a contracted delivery diameter and then self-expands to a larger diameter in situ to facilitate blood flow.

It is another object of the present invention to provide apparatus and methods for enhancing the flow of blood and emboli within a catheter by expanding the cross-sectional area of the catheter that extends from the site of the stenosis to the vascular entry site.

It is another object of the present invention to provide apparatus and methods for rapidly self-expanding the cross-sectional area of a catheter without relying on chemical or thermal transformations.

It is yet another object of the present invention to provide apparatus and methods for an expandable catheter whereby the structural integrity is not compromised upon expansion.

It is another object of the present invention to provide apparatus and methods for efficiently removing emboli by means of an occlusive member that is substantially flush with the vessel wall.

These and other objects of the present invention are accomplished by providing apparatus and methods suitable for removing emboli and facilitating blood flow within a catheter. The apparatus preferably comprises a catheter having a wire weave configuration, an elastomeric polymer coating covering the weave to provide a blood impermeable membrane, and an outer sheath covering the catheter in a contracted state. The catheter preferably comprises an occlusive distal section, a radially expanding main body, and a fixed diameter proximal section that passes through the vascular entry site.

In a preferred method, the catheter is advanced through the femoral artery and the distal end is positioned proximal to a lesion. As the outer sheath covering the catheter is retracted proximally, the occlusive distal section expands to a predetermined shape to form an occlusive seal against the vessel wall. As the outer sheath is further retracted, the main body of the catheter expands radially to a larger diameter. The outer sheath is further retracted proximally toward the vascular entry site, e.g., the arteriotomy.

The occlusive distal section occludes antegrade flow, and retrograde flow may be induced at the site of the stenosis, e.g., via negative pressure in a venous return line. An interventional procedure, such as angioplasty, stenting or atherectomy, then may be performed to treat the lesion. Emboli generated during the procedure are directed via the retrograde flow into the enlarged lumen of the catheter for subsequent removal.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1:
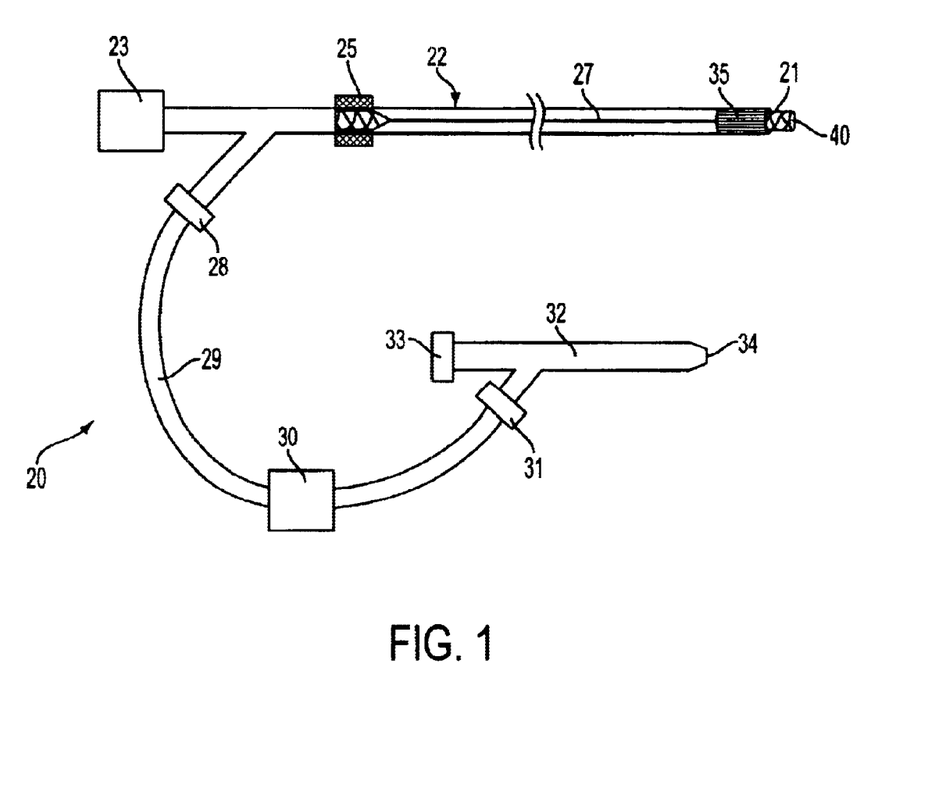
FIG. 1 is a side view of apparatus constructed in accordance with the present invention in a collapsed delivery state.

Referring to FIG. 1, embolic protection apparatus 20 constructed in accordance with principles of the present invention is described. Apparatus 20 comprises catheter 21, outer sheath 22, venous return line 32, tubing 29 and optional blood filter 30.

Catheter 21 comprises lumen 40 that communicates with hemostatic port 23, e.g., a Touhy-Borst connector and blood outlet port 28. Tubing 29 couples blood outlet port 28 to filter 30 and blood inlet port 31 of venous return line 32.

Outer sheath 22 preferably comprises clip 25, longitudinal slit 27 and solid distal section 35. Clip 25 is affixed to the proximal end of outer sheath 22 and may engage catheter 21 in a locked state, as shown in FIG. 1, or may disengage from catheter 21 when a force is applied. As described hereinbelow, longitudinal slit 27 permits outer sheath 22 to disengage from catheter 21, to allow proximal retraction of outer sheath 22 without interfering with blood outlet port 28 or hemostatic port 23.

Hemostatic port 23 and lumen 40 are sized to permit interventional devices, such as balloon angioplasty catheters, atherectomy devices and stent delivery systems, to be advanced through lumen 40 to the site of the occlusion.

Venous return line 32 includes hemostatic port 33, blood inlet port 31 and a lumen that communicates with ports 33 and 31 and tip 34. Venous return line 32 may be constructed in a manner per se known for venous introducer catheters. Tubing 29 may comprise a suitable length of a biocompatible material, such as silicone. Alternatively, tubing 29 may be omitted and blood outlet port 28 of catheter 21 and blood inlet port 31 of venous return line 32 may be lengthened to engage either end of filter 30 or each other.

Figure 2A:
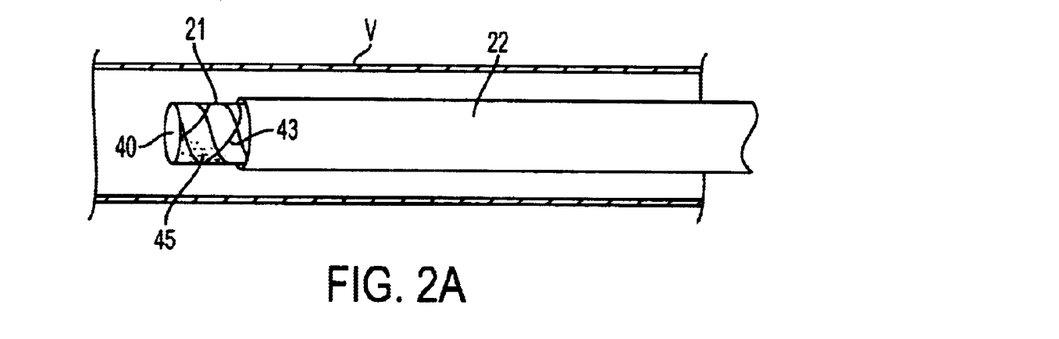
FIGS. 2A–2C are schematic illustrations of the expandable features of the catheter.

Referring to FIG. 2, the expandable features of catheter 21 are described in greater detail. FIG. 2A depicts catheter 21 having lumen 40 in a contracted state within outer sheath 22. The device may be transluminally inserted and positioned within a vessel V in the contracted state. The distal section of catheter 21 may be constructed in an expandable wire weave configuration. In a preferred embodiment, the wire weave comprises a shape-memory retaining material, for example, a Nickel Titanium alloy (commonly known in the art as Nitinol).

The use of Nitinol generally requires the setting of a custom shape in a piece of Nitinol, e.g., by constraining the Nitinol element on a mandrel or fixture in the desired shape, and then applying an appropriate heat treatments, which are per se known.

Figure 2B:
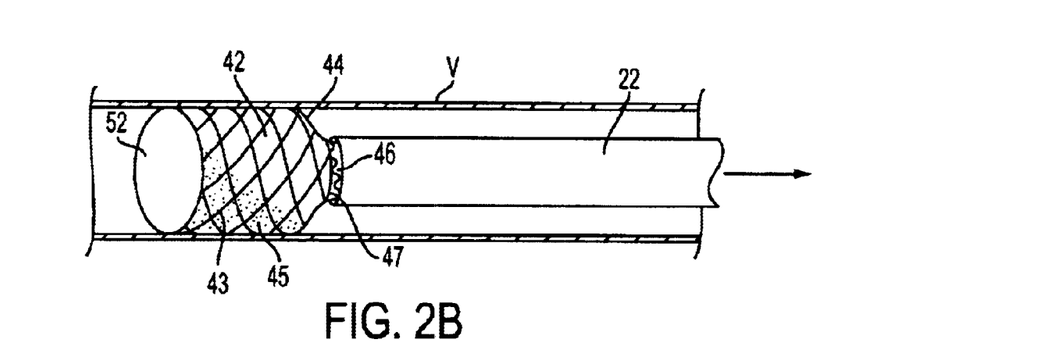

Catheter 21 preferably is enclosed by elastomeric polymer 45, such as latex, polyurethane or polyisoprene. The shape of catheter 21 is initially constrained by outer sheath 22. As outer sheath 22 is retracted proximally, wires 43 and lumen 40 expand radially and may expand linearly to form occlusive distal section 42 having mouth 52, as shown in FIG. 2B. Elastomeric polymer 45 stretches to conform to the expanded shape. The predetermined configuration preferably comprises angled taper 44 and hoop 47.

The radial expansion of occlusive distal section 42 is such that its outer diameter is substantially flush with the intima of vessel V to occlude antegrade flow. Additionally, the surface contact between occlusive distal section 42 and vessel V may effectively anchor the device.

Angled taper 44 facilitates direction of blood and emboli from mouth 52 into main body 46 of catheter 21. Additionally, angled taper 44 permits outer sheath 22 to slide distally over occlusive distal section 42 to effectively collapse that section within the sheath.

Figure 2C:
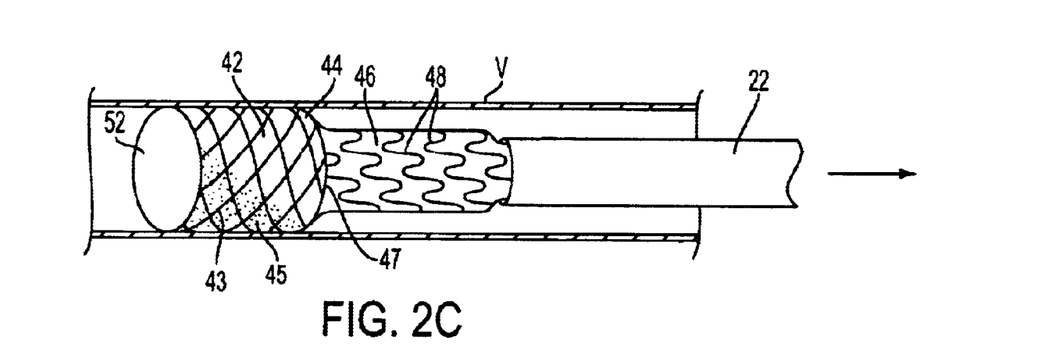

Hoop 47 may be used to separate occlusive distal section 42 from main body 46, as the two sections preferably have distinct expanded diameters. Main body 46 comprises a wire configuration that is initially compressed circumferentially within outer sheath 22. As outer sheath 22 is further retracted proximally, main body 46 expands radially within vessel V, as shown in FIG. 2C. Wires 48 expand radially to a predetermined shape that may be established, for example, by heat treating a shape-memory alloy as described hereinabove. Exemplary wire configurations for main body 46 are described in FIG. 5 hereinbelow.

Figure 3:
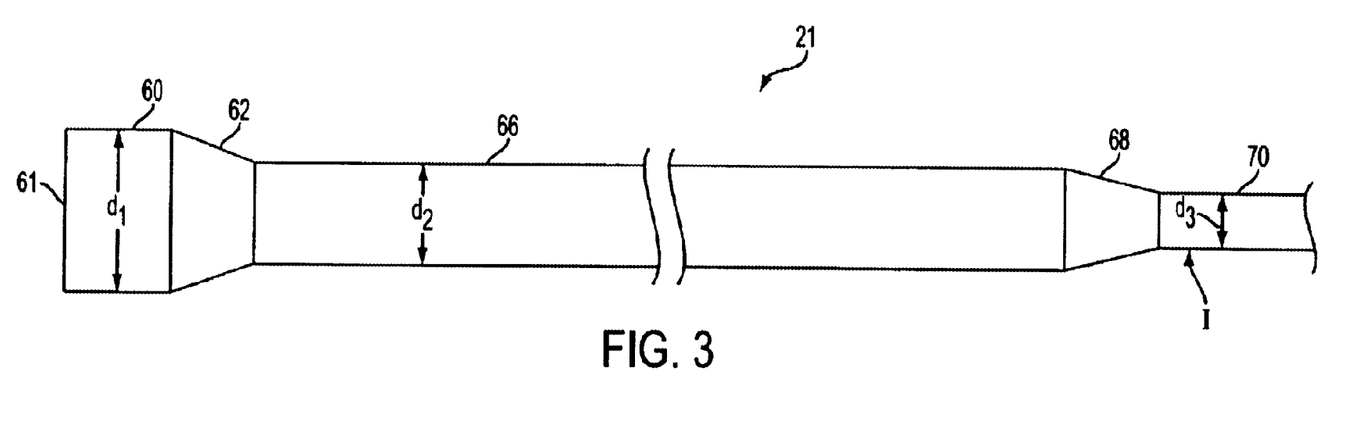
FIG. 3 is a side view of a catheter constructed in accordance with the present invention in a fully deployed state.

Referring now to FIG. 3, a schematic side view of catheter 21 is depicted in a fully deployed state. Catheter 21 comprises occlusive distal section 60, main body 66, proximal section 70, and angled tapers 62 and 68. Occlusive distal section 60 and main body 66 comprise expanded diameters $d_1$ and $d_2$, respectively, while proximal section 70 comprises transluminal insertion diameter $d_3$.

Occlusive distal section 60 and main body 66 are initially collapsed within outer sheath 22 such that their contracted diameters are substantially equal to the transluminal insertion diameter $d_3$ of proximal section 70. Catheter 21 then may be percutaneously and transluminally inserted into the body and maneuvered within the vasculature at diameter $d_3$ until deployed, as depicted in FIG. 2.

In the deployed state, $d_1$ is sized to occlude blood flow in the targeted vessel (other than through mouth 61). Diameter $_1$, may expand to occlude flow in a range of vessels. Occlusive distal section 60 facilitates removal of large emboli via mouth 61. Angled taper 62 assists in directing blood and emboli from occlusive distal section 60 into main body 66. Blood and emboli then are directed proximally at transport diameter $d_3$.

Advantageously, the enlarged lumen provided by main body 66 transports blood from a location near the lesion to a location slightly distal to vascular entry site I, a distance that preferably spans the majority of the overall length of catheter 21. Accordingly, flow resistance may be reduced throughout the majority of the catheter.

Angled taper 68 funnels blood from main body 66 into proximal section 70. Proximal section 70 preferably remains fixed at transluminal insertion diameter $d_3$ and extends from blood outlet port 28 to a location slightly distal to vascular entry site I.

Figure 4A:
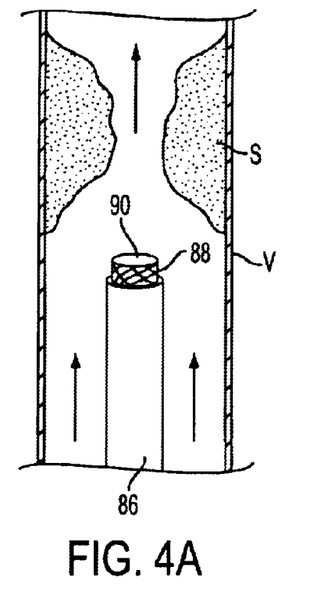
FIGS. 4A–4D depict method steps of using the catheter of the present invention.
Figure 4B:
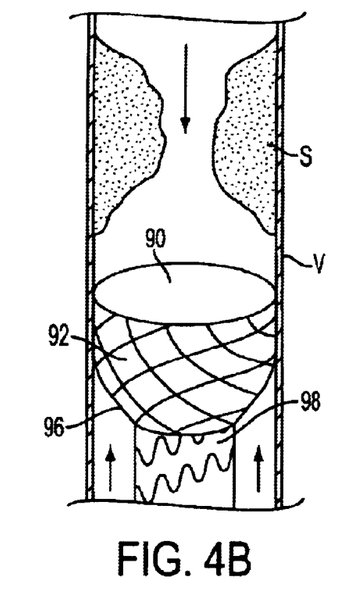

Referring to FIGS. 4A–4D, use of apparatus in accordance with the present invention is described. In FIG. 4, lesion S is located within a vessel V of the body. In a first step, catheter 88, initially compressed within outer sheath 86, is inserted either percutaneously and transluminally or via a surgical cut-down, to a position proximal to lesion S, as shown in FIG. 4A. As described hereinabove, outer sheath 86 then is retracted proximally to cause occlusive distal section 92 to deploy, as shown in FIG. 4B, and further retracted proximally to radially expand main body 98.

Venous return line 32 then may be introduced into the patient's femoral vein, either percutaneously or via a surgical cut-down. Filter 30 then is coupled between blood outlet port 28 of catheter 21 and blood inlet port 31 of venous return line 32 using tubing 29, and any air is removed from the line. Once this circuit is closed, negative pressure in venous return line 32 during diastole will establish a low rate continuous flow of blood through lumen 90 of catheter 21. As shown in FIG. 4B, the deployment of occlusive distal section 92 occludes antegrade flown in vessel V, while the negative pressure through lumen 90, e.g., from venous return line 32, induces retrograde flow at the site of the lesion.

This low rate continuous flow due to the difference between venous pressure and arterial pressure will continue throughout the interventional procedure. Specifically, blood passes through lumen 90 and blood outlet port 28 of catheter 21, through biocompatible tubing 29 to filter 30, and into blood inlet port 31 of venous return line 32, where it is reperfused into the remote vein. Continuous blood flow (except during inflation of any dilatation instruments) with reperfusion in accordance with the present invention provides efficient embolic removal with significantly reduced blood loss.

Figure 4C:
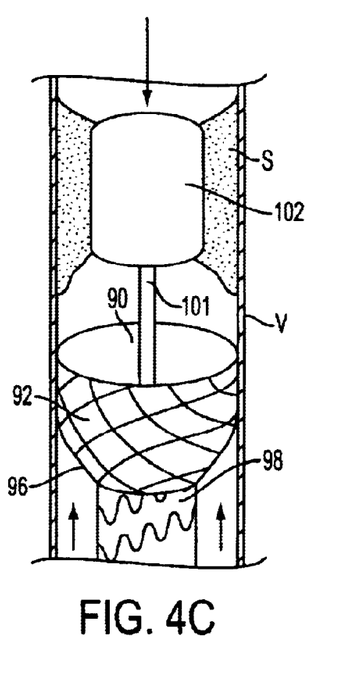

Referring to FIG. 4C, with occlusive distal section 92 deployed and retrograde flow established in vessel V, an interventional procedure to treat lesion S may be performed. The procedure may be any commonly known in the art. For example, balloon angioplasty may be applied whereby conventional angioplasty balloon catheter 101 having balloon 102 may be loaded through hemostatic port 23 and lumen 90, then positioned within lesion S. Hemostatic port 23 then is closed, and balloon 102 is inflated to treat lesion S. Balloon 102 then is deflated upon satisfactory removal or disruption of lesion S.

Figure 4D:
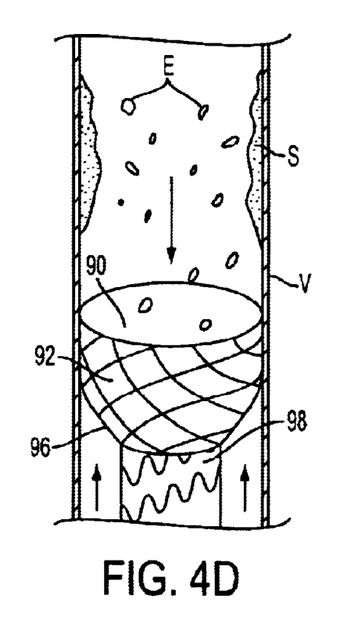

Referring to FIG. 4D, emboli E generated during the procedure are directed into lumen 90 via the established retrograde flow. Angled taper 96 funnels blood and emboli E into main body 98. Blood and emboli E travel proximally within catheter 21, and emboli E may be subsequently removed via filter 30.

Upon completion, outer sheath 86 may be advanced distally along the length of catheter 21 to collapse main body 98 and occlusive distal section 92 within the sheath, which in turn causes antegrade flow to become re-established in vessel V. Catheter 21 then may be retracted transluminally and the apparatus may be removed from the patient's vessel.

Figure 5A:
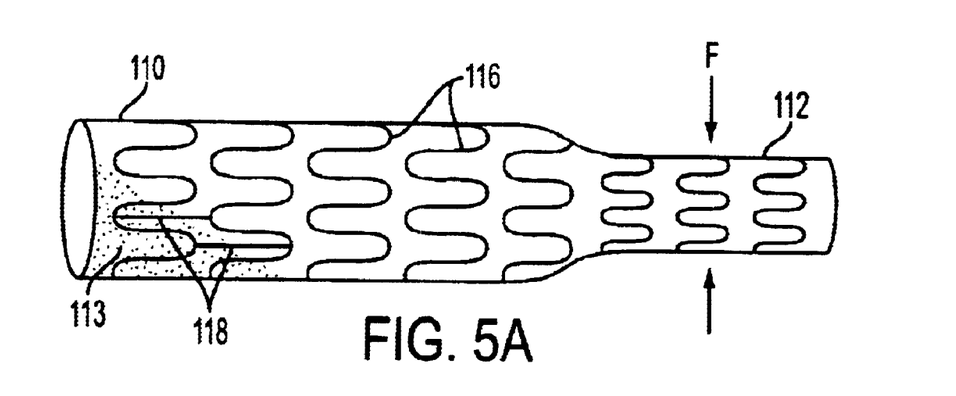
FIGS. 5A–5B illustrate alternative configurations of the expandable body of the catheter.

Referring to FIG. 5, alternative configurations of the radially expanding main body in accordance with the present invention are described. In FIG. 5A, a hoop configuration is shown wherein main body 110 of catheter 21 comprises several individual hoops 116. Individual hoops 116 are designed such that they may be compressed circumferentially by a compressive force F, e.g., the force provided by outer sheath 22, as depicted in region 112. When compressive force F is removed, hoops 116 expand to a larger, predetermined diameter. In a preferred embodiment, hoops 116 are manufactured from a shape-memory material, e.g, Nitinol, according to methods described hereinabove.

Individual hoops 116 preferably are enclosed within elastomeric polymer coating 113 to form an expandable, blood impermeable membrane. Individual hoops 116 may be connected to adjacent hoops via linkages 118 for additional structural stability.

Figure 5B:
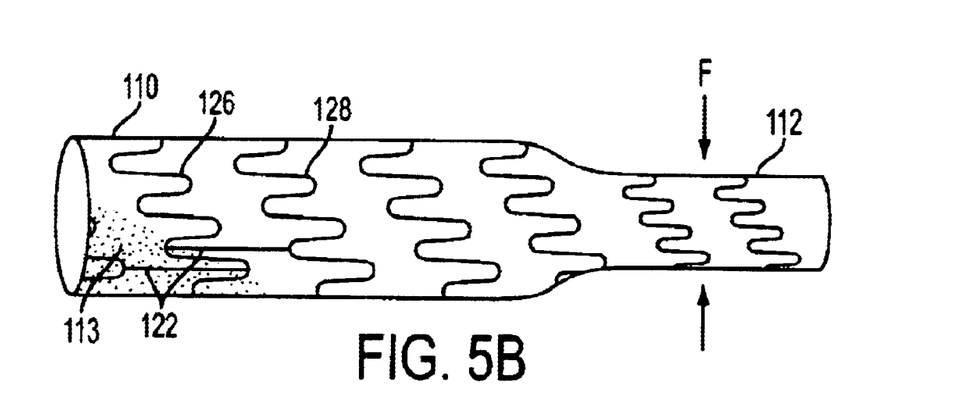

Alternatively, main body 110 may comprise a plurality of compressible, spiral-shaped wires. As shown in FIG. 5B, wires 126 and 128 are angled such that they form long, continuous spirals along the length of main body 110. The compressible, spiral-shaped wires preferably comprise a shape memory material and may be coated with elastomeric polymer 113. Linkages 122 may be used to provide additional support between adjacent spirals.

Referring now to FIG. 6, a mechanism for allowing proximal retraction of outer sheath 140 is described. Outer sheath 140 comprises clip 142, longitudinal slit 144 and solid distal section 146, as shown in FIG. 6A.

Figure 6A:
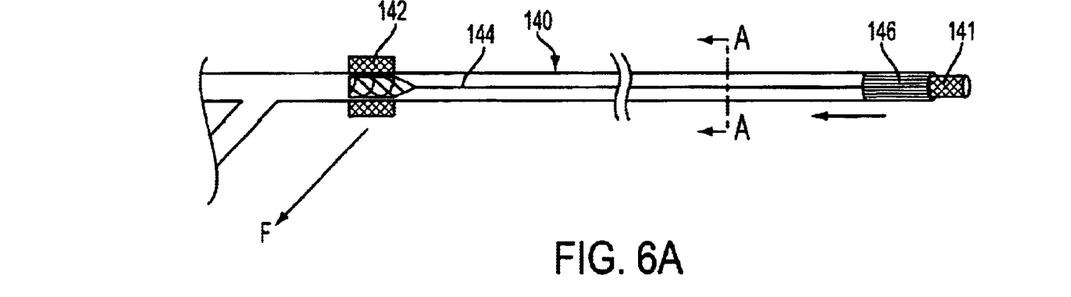
FIGS. 6A–6D describe a mechanism for enabling proximal retraction of the outer sheath of the present invention.
Figure 6B:
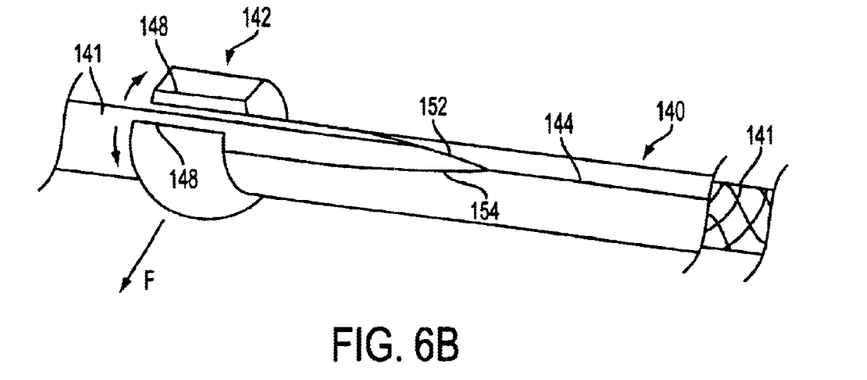

Clip 142 is sized to engage catheter 141 in a locked state, as shown in FIG. 6B. Clip 142 preferably comprises a compliant rubber-like material that may deform when a force F is applied in the direction indicated, i.e., a manual force applied by the physician. Walls 148 of clip 142 may part to allow clip 142 to disengage from catheter 141.

Figure 6C:
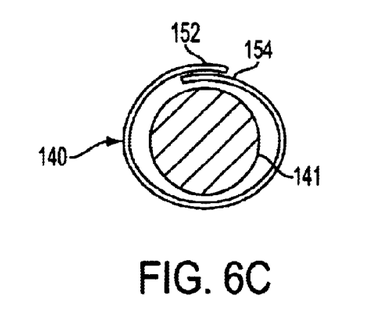
Figure 6D:
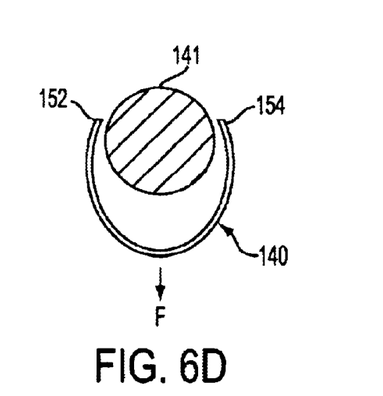

Longitudinal slit 144 of outer sheath 140 preferably comprises flaps 152 and 154. In a contracted state, flaps 152 and 154 overlap to enclose catheter 141, as shown in FIG. 6C from a sectional view through section line A—A of FIG. 6A. As a force F is applied, flaps 152 and 154 disengage from catheter 141, as shown in FIG. 6D from a sectional view through section line A—A.

Solid distal section 146 guides outer sheath 140 as it is further retracted proximally. When the procedure is completed, outer sheath 140 is advanced distally such that flaps 152 and 154 once again overlap. In this overlapping state, outer sheath 140 retracts catheter 141 within the sheath as the sheath is advanced distally. Clip 142 then may re-engage catheter 141.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. Apparatus suitable for removing emboli from a vessel, the apparatus comprising:

a catheter having a proximal section configured to extend outside a patient, a hemostatic port disposed on the proximal section, an occlusive distal section, a main body extending therebetween, and a lumen extending therethrough the catheter having a fluid impermeable cover; and an outer sheath disposed to slide longitudinally along the catheter;

wherein the main body has a contracted delivery diameter when disposed within the outer sheath and a radially expanded deployed diameter when deployed from the outer sheath.

2. The apparatus of claim 1 wherein the proximal section comprises a fixed diameter.

3. The apparatus of claim 1 wherein the occlusive distal section comprises a contracted state and an expanded state suitable for occluding flow in a vessel.

4. The apparatus of claim 3 wherein the occlusive distal section further comprises a wire weave configuration that forms a predetermined shape in the expanded state.

5. The apparatus of claim 4 wherein the predetermined shape of the occlusive distal section, when deployed, is substantially flush with the vessel wall at a distal portion and tapers in proximally to connect to the main body of the catheter.

6. The apparatus of claim 4 wherein the occlusive distal section comprises Nitinol.

7. The apparatus of claim 1 wherein the main body comprises a plurality of individually compressible hoops.

8. The apparatus of claim 7 wherein the main body consists of a nickel-titanium alloy.

9. The apparatus of claim 7 wherein the individually compressible hoops are enclosed within an elastomeric polymer coating.

10. The apparatus of claim 7 further comprising a plurality of linkages connecting the individually compressible hoops.

11. The apparatus of claim 1 wherein the main body comprises a spiral configuration having a plurality of compressible spiral-shaped wires.

12. The apparatus of claim 11 wherein the main body consists of a nickel-titanium alloy.

13. The apparatus of claim 11 wherein the compressible spiral-shaped wires are enclosed within an elastomeric polymer coating.

14. The apparatus of claim 11 further comprising a plurality of linkages connecting the compressible spiral-shaped wires.

15. The apparatus of claim 1 wherein the main body spans a greater distance than the proximal section.

16. The apparatus of claim 1 wherein the diameter of the main body in an expanded state is larger than the diameter of the proximal section.

17. The apparatus of claim 1 wherein the outer sheath is positioned in a distalmost position to compress the main body and occlusive distal section within the outer sheath.

18. A method for enhancing flow within a catheter, the method comprising:

providing a catheter disposed in a contracted state within an outer sheath, the catheter comprising a proximal section configured to extend outside a patient, a hemostatic port disposed on the proximal section, an occlusive distal section, a main body extending therebetween, and a lumen extending therethrough, the catheter having a fluid impermeable cover;

inserting the catheter and outer sheath into a patient's vasculature to a desired location; retracting the outer sheath proximally to deploy the occlusive distal section; and further retracting the outer sheath proximally to cause radial expansion of the main body.

19. The method of claim 18 further comprising:

performing an interventional procedure; and aspirating emboli generated during the interventional procedure into the lumen of the catheter.

20. The method of claim 19 further comprising:

at the conclusion of the interventional procedure, advancing the outer sheath to contract the main body and the occlusive distal section; and withdrawing the catheter and outer sheath from the patient's vasculature.

* * * * *